(12) United States Patent
Kopelman et al.

(10) Patent No.: US 6,334,853 B1
(45) Date of Patent: Jan. 1, 2002

(54) METHOD FOR OBTAINING A DENTAL OCCLUSION MAP

(75) Inventors: Avi Kopelman, Ramat-Chen; Baruch Nissenbaum, Ramat Gan, both of (IL)

(73) Assignee: Cadent LTD, Or Yehuda (IL)

( * ) Notice: Subject to any disclaimer, the term of this patent is extended or adjusted under 35 U.S.C. 154(b) by 0 days.

(21) Appl. No.: 09/424,195

(22) PCT Filed: May 14, 1998

(86) PCT No.: PCT/IL98/00219

§ 371 Date: Jun. 12, 2000

§ 102(e) Date: Jun. 12, 2000

(87) PCT Pub. No.: WO98/52493

PCT Pub. Date: Nov. 26, 1998

(30) Foreign Application Priority Data

May 22, 1997 (IL) ........................................ 120892

(51) Int. Cl.⁷ .................................................. A61B 5/103
(52) U.S. Cl. ........................... 600/590; 600/587; 433/214
(58) Field of Search .................................. 600/587, 590; 33/511, 512, 513; 433/68, 69, 214, 229; 128/898

(56) References Cited

U.S. PATENT DOCUMENTS

| | | | |
|---|---|---|---|
| 4,799,785 A | | 1/1989 | Keates et al. ................ 351/212 |
| 4,983,120 A | * | 1/1991 | Coleman et al. ............... 433/24 |
| 5,458,487 A | * | 10/1995 | Komatsu et al. ............... 433/71 |
| 5,605,459 A | * | 2/1997 | Kuroda et al. ................ 433/214 |
| 5,730,151 A | * | 3/1998 | Summer et al. ............... 600/587 |
| 5,977,979 A | * | 11/1999 | Clough et al. ............... 345/422 |
| 5,989,199 A | * | 11/1999 | Cundari et al. .............. 600/587 |

FOREIGN PATENT DOCUMENTS

| | | | |
|---|---|---|---|
| EP | 0 593 061 | 4/1994 | ........... A61C/19/05 |
| WO | WO 97/03622 | 2/1997 | |

OTHER PUBLICATIONS

International Search Report for PCT/IL98/00219, dated Aug. 31, 1998 (2 pgs.).
Rakoski, Thomas, et al., "Study Cast Analysis," Color Atlas of Dental Medicine/Orthodontic–Diagnosis, p. 207, published by Thieme Medical Publishers, N. Y.

* cited by examiner

*Primary Examiner*—Robert L. Nasser
*Assistant Examiner*—Charles Marmor, II
(74) *Attorney, Agent, or Firm*—Fitch, Even, Tabin & Flannery

(57) ABSTRACT

A method for obtaining a dental occlusion map of a three-dimensional virtual computer model of teeth of upper and lower jaws of a mouth. The occlusion map indicates the distances between opposite regions on facing surfaces of opposite teeth of the upper and lower jaws of the mouth. The method includes the steps of determining the distances between opposite regions on opposite teeth of the upper and lower jaws of the mouth, and setting up a correspondence between the determined distances and regions on a mapping surface.

13 Claims, 4 Drawing Sheets

○ ○ ○ ○
40  42  44  46

○ ○ ○ ○
40  42  44  46

○ ○ ○ ○
50  52  54  56

○ ○ ○ ○
60  62  64  66

○ ○ ○ ○
70  72  74  76

METHOD FOR OBTAINING A DENTAL OCCLUSION MAP

FIELD OF THE INVENTION

The invention relates to dental occlusion relations for the distances between teeth.

BACKGROUND OF THE INVENTION

In dental procedures in general and more specifically in orthodontic procedures, a model of a patient's teeth is required in order to make treatment decisions in, for example, design of braces, crowns, bridges, etc., and to allow monitoring of dental procedures. Of particular importance is a knowledge of the distance and spatial relationship between the teeth on opposite jaws.

Dental procedures requiring knowledge of the position of teeth and the distance between teeth on opposite jaws, generally use models of the teeth, referred to hereinafter as "dental models". Typically, plaster dental models are used, which are made by casting plaster into the negative impression made by teeth in an appropriate matrix. Dental models can, however, be made of any convenient material.

However, this approach has a number of major drawbacks. First, in the occluded state it is difficult to see the relation between facing surfaces of opposite teeth of the upper and lower jaws. Second, on moving a tooth, or adding a tooth, or changing the form of a tooth in the dental model, it is not possible to see if the affected tooth affects the occlusion. Third, the information provided by dental models regarding proximity of opposite teeth in opposite jaws is typically no more than whether certain points of opposite teeth make contact, or not, in the occluded state. In order to be able to arrive at an optimal closing of the teeth when changes are made to one or more of the teeth of the dental model, a fairly long and tiresome process of physically modelling the affected teeth is required in order to ensure a good fit between opposite teeth on opposite jaws in the occluded state.

With the advent of powerful computers and advanced computer aided design techniques, it would be expected that three dimensional virtual dental models would help in alleviating the problems encountered with the plaster dental models. Storing a computer virtual dental model on a computer can be achieved "directly" by scanning and digitizing the teeth and gums, or "indirectly" by utilizing a plaster dental model or the negative impression. The latter method is disclosed in PCT Application No. PCT/IL 96/00036, Publication No. WO 97/03622, published on Feb. 6, 1997, hereinafter incorporated by reference. However, none of the existing virtual computer dental models provide tools relating to the distance between opposite teeth on opposite jaws.

SUMMARY OF THE INVENTION

It is the object of the present invention to provide a method for graphically representing the distance between opposite points, or regions, on the surface of opposite teeth of the upper and lower jaws. The proposed method exploits an existing three-dimensional virtual dental model obtained, directly or indirectly, from actual teeth and associated gums.

The resulting graphical representation of the distance between opposite points, or regions, on the surface of opposite teeth will be termed an "occlusion map".

The occlusion map comprises colored regions, where each color corresponds to a given distance, or range of distances, between opposite points or regions on the surface of opposite teeth. The occlusion map therefore provides a clear indication of the distance between opposite portions of the surfaces of opposite teeth. The term "color" used herein includes not only all colors and shades of colors but also black and white and all shades of grey between black and white on a grey scale.

In accordance with the present invention there is provided a method for obtaining a dental occlusion map of a three-dimensional virtual computer model of teeth of upper and lower jaws of a mouth, said occlusion map indicative of distances between opposite regions on facing surfaces of opposite teeth of the upper and lower jaws of the mouth, said method comprising the steps of:

(i) determining said distances between opposite regions on opposite teeth of the upper and lower jaws of the mouth; and (ii) setting up a correspondence between said determined distances and regions on a mapping surface.

If desired, said mapping surface is a plane, whereby said dental occlusion map is a two-dimensional map of the distances between said opposite regions on said opposite teeth.

Alternatively, said mapping surface is a facing surface of said facing surfaces of opposite teeth of the upper and lower jaws of the mouth.

In accordance with one embodiment, said facing surface belongs to the teeth of said upper jaw, and said lower teeth and lower jaw are transparent.

In accordance with another embodiment, said facing surface belongs to the teeth of said lower jaw, and said upper teeth and upper jaw are transparent.

Preferably, said opposite regions on said facing surfaces of opposite teeth are colored in accordance with a given color scale and wherein each color corresponds to a given distance.

Alternatively, said opposite regions on said facing surfaces of opposite teeth are shaded in accordance with a grey scale and wherein each shade corresponds to a given distance.

If desired, said opposite regions on said facing surfaces of opposite teeth are points.

Further if desired, said regions on said mapping surface comprise at least one pixel.

By one specific application, said occlusion map only shows those distances that are less than one tenth of a millimeter.

By another specific application, said occlusion map only shows those distances that are zero in value.

BRIEF DESCRIPTION OF THE DRAWINGS

For a better understanding, the invention will now be described, by way of example only, with reference to the accompanying drawings in which.

DETAILED DESCRIPTION OF THE INVENTION

Figure 1:
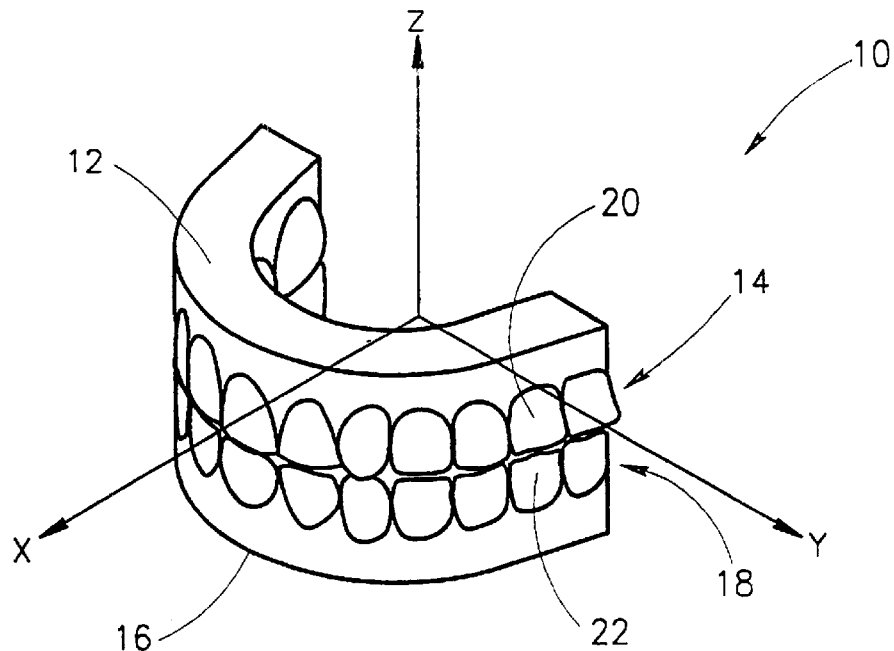
FIG. 1 shows an illustrative perspective view of a virtual image dental model in the occluded state.

Attention is first drawn to FIG. 1 showing an illustrative perspective view of a virtual image dental model 10 in the occluded state. Superimposed on dental model 10 is a rectangular Cartesian coordinate system XYZ with the XY-plane coinciding with the "occlusion plane". The occlusion plane is defined as the horizontal plane through the tips of the buccal cusps of the premolars or the tips of the mesiobuccal cusps of the first molars and first premolars (see Thomas Rakoski, Irmtrud Jones and Thomas M. Graber. "Color Atlas of Dental Medicine, Orthodontic-Diagnosis, page 207, published by Thieme Medical Publishers, New York 1993). As will be described in greater detail below, the occlusion plane is used as a reference plane for defining a grid system used in the invention. Shown in the figure are upper jaw 12 with upper teeth 14 and lower jaw 16 with lower teeth 18. Shown in particular are a pair of opposite teeth, namely upper tooth 20 and lower tooth 22.

Figure 2:
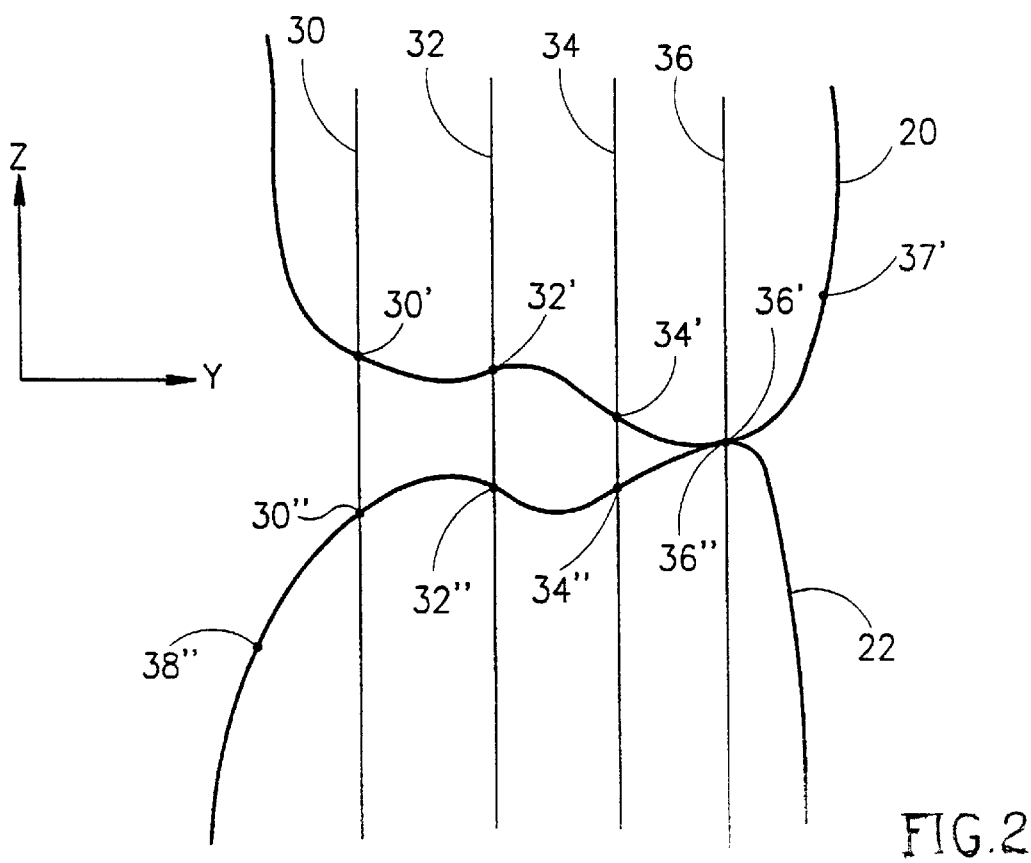
FIG. 2 shows four opposite points in a cross-sectional view through an upper tooth and an opposite lower tooth taken in the ZY-plane at an arbitrary value of X.

FIG. 2 shows four opposite points in a cross-sectional view through upper tooth 20 and opposite lower tooth 22, of FIG. 1. The actual position at which the cross-section is taken is of no importance since the figure is for illustrative purposes only. The cross-section is taken at an arbitrary value along the X-axis and parallel to the ZY-plane. It should be noted that since teeth 20 and 22 are at the rear of the jaws the buccal and lingual sides of the teeth are substantially perpendicular to the Y-axis and therefore it is convenient to consider a cross-section parallel to the ZY-plane. However, for other teeth it may be more convenient to choose a cross-sectional plane passing through the Z-axis and making an arbitrary angle with the Y axis. Shown are four parallel grid lines 30, 32, 34 and 36. These grid lines are parallel to the Z-axis, or, equivalently perpendicular to the occlusion plane (not shown). Only four grid lines have been shown for illustrative simplicity. Grid lines 30, 32, 34 and 36 and the curve representing the cross-section of the surface of upper tooth 20 cross at points 30', 32', 34' and 36', respectively. Similarly, grid lines 30, 32, 34 and 36 and the curve representing the cross-section of the surface of lower tooth 22 cross at points 30", 32", 34" and 36", respectively.

Each of the two points of the pairs of opposite points (30', 30"), (32', 32"), (34', 34") and (36', 36") has the same (X, Y) coordinates but a different Z coordinate, depending on the relative separation of the opposite points of each pair. It should be kept in mind that the cross-sectional view shown in the figure is obtained from virtual image dental model 10. Hence, the curves representing the cross-sections of the surfaces of the upper and lower teeth are actually made up of many discrete points. Hence, the number of parallel grid lines could, if desired, be equal to the number of pairs of points of the virtual computer model, comprising the upper and lower curves representing the cross-sections of the surfaces of the upper and lower teeth.

It should also be noted that only those points on opposite teeth which have an opposite facing point are taken into account for distance determinations. A point such as 37' on upper tooth 20 has no opposite point on lower tooth 22. That is, a grid line passing through point 37' on upper tooth 20 will not cut the curve representing the cross-section of the surface of lower tooth 22. Hence, point 37' has no "facing partner" on lower tooth 22 which if it had, would be numbered 37". Similarly, point 38" on lower tooth 22 has no "facing partner" on upper tooth 20. Hence, points having a "facing partner" such as points 30', 32', 34' and 36' on the surface of upper tooth 20 lie on a "facing surface" of the surface of upper tooth 20, similarly points 30", 32", 34" and 36" on the surface of lower tooth 22 lie on a "facing surface" of the surface of lower tooth 22. Clearly, points such as 37' on upper tooth 20 that do not have a "facing partner" on the surface of lower tooth 22 do not lie on the "facing surface" of upper tooth 20. Likewise, points such as 38" on lower tooth 22 that do not have a "facing partner" on the surface of upper tooth 20 do not lie on the "facing surface" of lower tooth 22.

Since the coordinates of all points comprising the virtual image dental model are known, the distances between opposite points on the grid line can easily be determined. Let the distance between point I' on the surface of upper tooth 20 and its "facing partner" point I" on the surface of lower tooth 22, be denoted by d(I',I"), then $$d(I',I'')=|Z(I')-Z(I'')|,$$

where Z(I'), Z(I") are the Z coordinates of the points I', I", respectively. The absolute value of the difference between the coordinates has been taken since only the magnitude of the difference is of interest. For example, the distance between opposite points 30' and 30" on the upper and lower teeth 20 and 22, respectively, is given by $$d(30',30'')=|Z(30')-Z(30'')|.$$

In this manner the distances between the other three pairs of points (32' 32"), (34',34") and (36',36") are found. Each of the four values of distance so obtained is then related to a corresponding shade on a grey scale, or a corresponding color on a color scale.

As a non-binding example let the distances found correspond to colors as follows:

d(30',30")=red, d(32',32")=orange, d(34',34")=yellow, and d(36',36")=blue.

Figures 3, 4, 5:
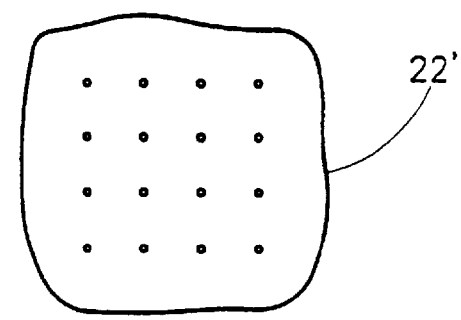
FIG. 3 shows a map onto a line of the distances between the four opposite pairs of points shown in FIG. 2.
FIG. 4 shows a map onto a plane of the distances between four opposite pairs of points in four different parallel cross-sectional planes taken parallel to the ZY-plane at different values of X.
FIG. 5 shows a map of the distances of FIG. 4 (on a smaller scale) superimposed on the outline of the plan view of the lower tooth in FIG. 2 looking in the negative Z direction.

The above four distances are then represented by a map of colored dots, or pixels, as shown in FIG. 3. Pixel 40 is red, pixel 42 is orange, pixel 44 is yellow and pixel 46 is blue. The distance between each pixel is equal to the distance between each grid line in FIG. 2, and the order of the pixels in FIG. 3 is the same as the order as that of the corresponding opposite pairs of points in FIG. 2. That is, the distance d(30',30") corresponds to pixel 40, the distance d(32',32") corresponds to pixel 42, the distance d(34',34") corresponds to pixel 44 and the distance d(36',36") corresponds to pixel 46. In other words, the values of the distances between opposite pairs of points on opposite upper and lower teeth are mapped onto colored pixels on a straight line with the distance between adjacent pixels equal to the distance between adjacent grid lines on which the adjacent pairs of opposite points corresponding to the adjacent pixels are situated. For example, the distance between pixel 40 and pixel 42 is equal to the distance between grid line 30 on which the opposite pair of points (30',30") are situated and grid line 32 on which the opposite pair of points (32',32") are situated.

The process described above for generating the line of pixels shown in FIG. 3 is now repeated for another cross-section of teeth 20 and 22. Preferably, but not necessarily, the new cross-section is parallel to the cross-section shown in FIG. 2. The new cross-section is preferably, but not necessarily, distanced from the cross-section shown in FIG. 2 by a distance equal to the distance between the grid lines shown in FIG. 2. Repeating the process described above in the new cross-section gives rise to a new line of colored pixels 50, 52. 54 and 56, representing the distances between four pairs of opposite points on the upper and lower teeth in the new cross-section.

The above process is repeated for another cross-section, giving rise to another line of colored pixels 60, 62, 64 and 66, and is then yet repeated for another cross-section giving rise to yet another line of colored pixel 70, 72, 74 and 76. The result of this process is shown in FIG. 4 showing a map of the 16 colored pixels 40, 42, . . . , 74, 76 onto a plane. Again, the distance between neighboring pixels is equal to the distance between neighboring grid lines on which the adjacent pairs of points corresponding to the adjacent pixels are situated.

Although FIG. 4 shows a 4 by 4 matrix of pixels as obtained from four cross-sections of the opposite pairs of teeth in FIG. 2, with four grid lines in each cross-section, this is just an illustrative example. In general, there will be many more grid lines and many more cross-sections. In fact, grid lines can be drawn through each generating the virtual image dental model 10. The grid lines are all parallel to each other and are preferably perpendicular to the occlusion plane. It is in this sense that the occlusion plane acts as a reference plane for the grid lines, as mentioned above.

In the illustrative example described above the number of cross-sections for the opposite pair of teeth 20, 22 was taken to be equal to the number of grid lines in the first cross-section chosen. However, this was done merely for illustrative purposes. In general, the matrix of pixels obtained (as shown in FIG. 4) will not be square. Also, since teeth are, in general, irregular in shape and since opposite teeth do not, in general, completely overlap the number of pixels per row will, in general, differ from row to row. For example, if the pixel map shown in FIG. 4 was generated from another pair of opposite teeth, it is quite possible that pixel 56 would be missing in the second row of the matrix and that, for example, pixel 70 in the fourth row would also be missing.

The map of distances between pairs of opposite points on opposite teeth, such as that shown in FIG. 4 will be referred to as an "occlusion map" for the opposite pair of teeth. It is often convenient to superimpose an occlusion an opposite pair of teeth on the outline of one, or both, of the teeth of the pair. FIG. 5 shows the occlusion map of FIG. 4 superimposed on outline 22" of the plan view of lower tooth 22 looking in the negative Z direction. Clearly, in this case, the points comprising the occlusion map are mapped onto the facing surface of lower tooth 22. In the same manner, the points comprising the occlusion map can be mapped onto the facing surface of upper tooth 20.

Figure 6:
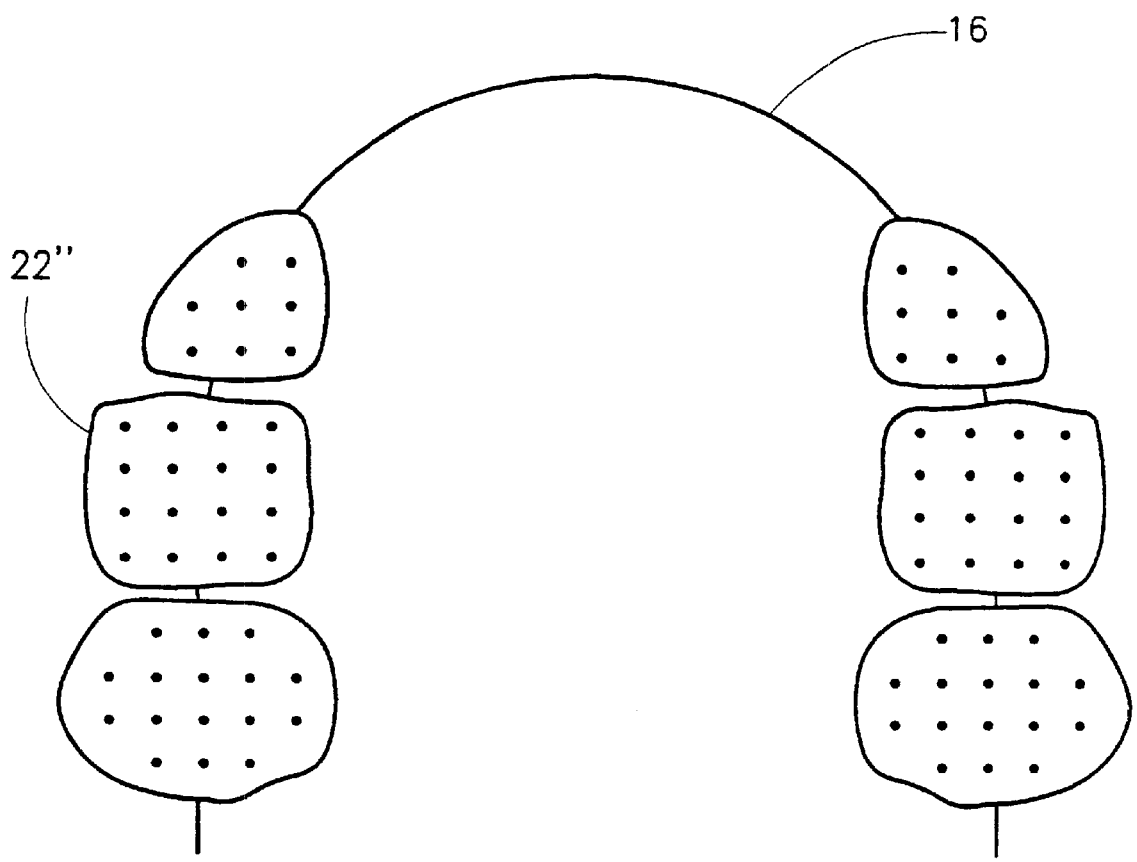
FIG. 6 shows an occlusion map for the three posterior teeth on both sides of the virtual image dental model, shown in FIG. 1, superimposed on the outline of the plan view of the teeth of the lower jaw looking in the negative Z direction.

Attention is now drawn to FIG. 6, showing an occlusion map of the rear three teeth on both sides of the mouth superimposed on the outline of the plan view of the teeth of lower jaw 16, looking in the negative Z direction. It should be clear that the occlusion map could just as well have been superimposed on the outline of the plan view of the teeth of upper jaw 12 looking in the positive Z direction.

Furthermore, the occlusion map could be superimposed on the outline of the plan view of the teeth of both the upper and lower jaws and set side by side. This affords easy monitoring of dental procedures by allowing a dental surgeon, orthodontist or dentist to see the relationship between the surfaces of opposite teeth (i.e. the distances between opposite pairs of points on opposite teeth) with the jaws closed, by studying the dental occlusion map with respect to both the upper and lower teeth. A tooth (or teeth) can be fitted with a crown (or a bridge), or a tooth can be moved in the virtual three-dimensional computer image of the dental model and the influence of the change made on the relationship between opposite teeth on the upper and lower jaws can be seen by noting color changes in the dental occlusion map. Changes can continue to be made until a desired spatial relationship between opposite teeth is achieved. This type of procedure would clearly be very difficult, or almost impossible, to perform on a plaster model of the teeth.

In another embodiment of the invention, the occlusion map is superimposed directly on the surface of the three-dimensional virtual image of the teeth. For example, the occlusion map can be superimposed on the teeth of the lower jaw. The lower jaw itself will be colored by some color not included in the occlusion map. In this embodiment, the upper jaw and teeth can either be transparent, but observable or not present al all. The virtual image can be rotated so that on "looking down" at the lower jaw through the transparent upper jaw, the occlusion map on the background of the surface of the lower teeth can clearly be seen. What actually will be seen, is very similar to the result shown in FIG. 6.

Similarly, the procedure can be reversed and the occlusion map can be superimposed on the teeth of the upper jaw. In this case the upper jaw will be made opaque and the lower jaw and teeth will be transparent or not present at all. Again, the three-dimensional virtual image can be rotated so that on "looking up" at the upper jaw through the transparent lower jaw the occlusion map on the background of the upper teeth can be seen. Again, the result is similar to that shown in FIG. 6. In both theses cases the resulting distance map will also be termed an "occlusion map", since it is also a map of the distance between opposite teeth. The occlusion map in this case is not planar but takes on the topography of the surface of the onto which it is superimposed.

Figure 7:
FIG. 7 shows a map onto a line of the distances between the four opposite pairs of points shown in FIG. 2, whereby each determined distance is mapped onto four pixels.

Several embodiments of the foregoing described method for obtaining a dental occlusion map exist. In accordance with one embodiment, each determined distance d(I',I") is mapped onto several pixels. This is contrary to the mapping of each determined distance onto one pixel as illustrated in FIG. 3 for one cross-section and FIG. 4 for four cross-sections. For example, each determined distance d(I',I") could be mapped onto four pixels as shown in FIG. 7 for one cross-section.

Figure 8:
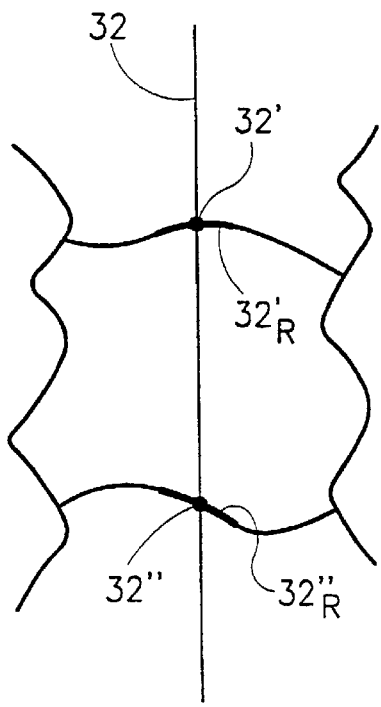
FIG. 8 shows a partial cross-sectional view through an upper tooth and an opposite lower tooth with two opposite points shown, each point being surrounded by a small region.

In accordance with another embodiment, each determined distance d(I',I") represents the distance between opposite pairs of surface regions on opposite teeth. FIG. 8 shows a partial cross sectional view through tooth 20 and lower tooth 22 around points 32' and 32" of FIG. 2. As shown, each point is surrounded by a small region. Point 32' is surrounded by region $32'_R$ and point 32" is surrounded by region $32''_R$. What is seen in FIG. 8 is the cross sections of regions $32'_R$ and $32''_R$. These regions can be circular, elliptic, or irregular in shape. Furthermore, the points 32' and 32" do not have to be located at the geometric center of the regions $32'_R$ and $32''_R$. In a manner similar to that described for pairs of points of opposite teeth, regions having a "facing partner" such as regions $30'_R$, $32'_R$, $34'_R$ and $36'_R$ on the surface of upper tooth 20 lie on a "facing surface" of the surface of upper tooth 20, similarly regions 30″$_R$, 32″$_R$, 34″$_R$ and 36″$_R$ on the surface of lower tooth 22 lie on a "facing surface" of the surface of lower tooth 22.

The distance d(32′,32″) between the points 32′ and 32″ is taken to represent the distance between the regions 32′$_R$ and 32″$_R$, that is d(32′$_R$,32″$_R$)=d(32′,32″). For a given cross-section, each of the determined distances d(I′$_R$,I″$_R$) between the regions I′$_R$ and I″$_R$ (e.g., I=, 30, 32, 34 and 36, as in FIG. 2) can then be mapped onto one pixel, as shown in FIG. 3, or onto several pixels, e.g. four pixels as shown in FIG. 7.

The above two described embodiments are particularly useful when the grid lines are not dense, in which case the resulting matrix of pixels is sparse giving rise to an occlusion map of widely spaced pixels making it difficult to see the resulting color variation in the occlusion map.

Figure 9:
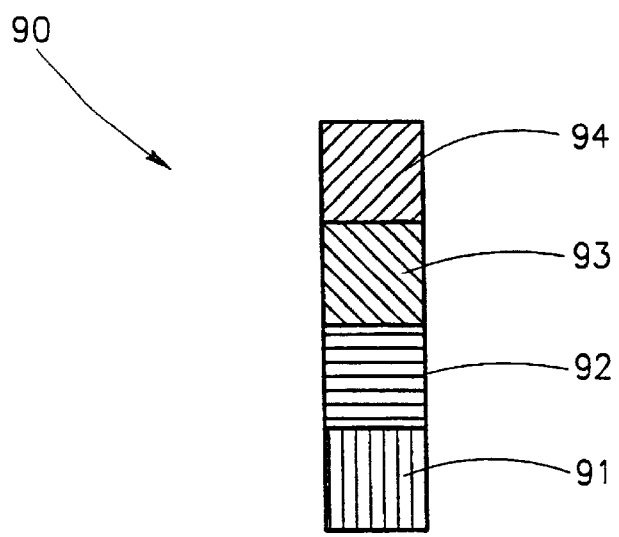
FIG. 9 shows an illustrative example of a color code key.

In practice, it is useful to provide a color code key for relating the colors observed in an occlusion map to the distances between opposite pairs of surface regions (or points) on opposite teeth. An illustrative example of a convenient color code key is shown in FIG. 9. In this example, color code key 90 comprises four colors 91, 92, 93 and 94. Each color can either represent a given distance, or a range of distances. For example, in the former case, color 91 may indicate 0.3 mm and color 93 may indicate a distance of 2 mm. Whereas in the latter case, color 91 may indicate the range of distances 0.3 to 2 mm and color 92 may indicate the range of distances 2.1 to 4 mm.

For convenience, the color code key is placed along side the occlusion map, allowing the user to easily relate the colored regions of the occlusion map to distances.

Although the present invention for graphically representing the distances between opposite pairs of regions or points has been described with respect to teeth it is contemplated that the inventive technique set forth herein is usable and workable with respect to other objects having facing surfaces, and can without undue modification or experimentation be applied to other objects that would benefit from such techniques. Furthermore, the method is not bound to representing the distances between the surfaces of opposite teeth by colors (or shades of grey), albeit a very convenient graphical aid providing the user with an straightforward and clear understanding if the distance relation between the surfaces of opposite teeth.

Therefore, although the present invention has been described to a certain degree of particularity, but it should be understood that various alterations and modifications can be made without departing from the spirit or scope of the invention as hereinafter claimed.

What is claimed is:

1. A method for obtaining a dental occlusion map of a three-dimensional virtual computer model of teeth of upper and lower jaws of a mouth, said occlusion map indicative of distances between opposite regions on facing surfaces of opposite teeth of the upper and lower jaws of the mouth, said method comprising the steps of:

(i) determining said distances between opposite regions on opposite teeth of the upper and lower jaws of the mouth; and (ii) setting up a correspondence between said determined distances and regions on a mapping surface.

2. The method for obtaining a dental occlusion map in accordance with claim 1, wherein said mapping surface is a plane, whereby said dental occlusion map is a two-dimensional map of the distances between said opposite regions on said opposite teeth.

3. The method for obtaining a dental occlusion map in accordance with claim 1, wherein said mapping surface is a facing surface of said facing surfaces of opposite teeth of the upper and lower jaws of the mouth.

4. The method for obtaining a dental occlusion map in accordance with claim 3, wherein said facing surface belongs to the teeth of said upper jaw, and said lower teeth and lower jaw are transparent.

5. The method for obtaining a dental occlusion map in accordance with claim 3, wherein said facing surface belongs to the teeth of said upper jaw, and said lower teeth and lower jaw are not present.

6. The method for obtaining a dental occlusion map in accordance with claim 3, wherein said facing surface belongs to the teeth of said lower jaw, and said upper teeth and upper jaw are transparent.

7. The method for obtaining a dental occlusion map in accordance with claim 3, wherein said facing surface belongs to the teeth of said lower jaw, and said upper teeth and upper jaw are not present.

8. The method for obtaining a dental occlusion map in accordance with claim 1, wherein said opposite regions on said facing surfaces of opposite teeth are shaded in accordance with a grey scale and wherein each shade corresponds to a given distance.

9. The method for obtaining a dental occlusion map in accordance with claim 1, wherein said opposite regions on said facing surfaces of opposite teeth are colored in accordance with a given color scale and wherein each color corresponds to a given distance.

10. The method for obtaining a dental occlusion map in accordance with claim 1, wherein said opposite regions on said facing surfaces of opposite teeth are points.

11. The method for obtaining a dental occlusion map in accordance with claim 1, wherein said regions on said mapping surface comprise at least one pixel.

12. The method for obtaining a dental occlusion map in accordance with claim 1, wherein said occlusion map only shows those distances that are less than one tenth of a millimeter.

13. The method for obtaining a dental occlusion map in accordance with claim 1, wherein said occlusion map only shows those distances that are zero in value.

* * * * *